United States Patent
Huang et al.

(10) Patent No.: US 8,278,078 B2
(45) Date of Patent: Oct. 2, 2012

(54) METHOD OF CULTIVATING YEAST FOR ENHANCING PENTITOL PRODUCTION

(75) Inventors: Chiung-Fang Huang, Taipei (TW); Wei-Hsi Chen, Taipei (TW); Ting-Hsiang Lin, Taoyuan County (TW); Wen-Heng Chen, Taoyuan County (TW); Gia-Luen Guo, Taipei County (TW); Wen-Song Hwang, Taoyuan County (TW)

(73) Assignee: Atomic Energy Council-Institute of Nuclear Energy Research, Lungtan, Taoyuan (TW)

( * ) Notice: Subject to any disclaimer, the term of this patent is extended or adjusted under 35 U.S.C. 154(b) by 209 days.

(21) Appl. No.: 12/790,484

(22) Filed: May 28, 2010

(65) Prior Publication Data

US 2011/0104772 A1    May 5, 2011

(30) Foreign Application Priority Data

Oct. 30, 2009  (TW) ................ 98136801 A

(51) Int. Cl.
*C12P 7/18* (2006.01)
*C12N 1/18* (2006.01)

(52) U.S. Cl. .................................................. 435/158

(58) Field of Classification Search .............. 435/158, 435/254.23

See application file for complete search history.

(56) References Cited

OTHER PUBLICATIONS

Toivari et al., Appl. Environ. Microbiol. 73(17) 5471-5476 (2007).*

* cited by examiner

*Primary Examiner* — Chih-Min Kam
(74) *Attorney, Agent, or Firm* — Jackson IPG PLLC

(57) ABSTRACT

A method for culturing the yeast for enhancing pentitol production is provided. The yeast cultured according to the present disclosure is *Pichia stipitis*. Application of the yeast in pentitol production by fermention of the lignocellulosic hydrolysate or the xylose-to-pentitol production yield can be enhanced 3 to 6 times from the non-detoxified or the over-liming-processed lignocellulosic hydrolysate.

6 Claims, 8 Drawing Sheets

| Concentration (g/L) | |
|---|---|
| Glucose | 8.72 |
| Xylose | 29.97 |
| Arabinose | 6.75 |
| Acetic Acid | 3.01 |
| Furfural | N/A |
| HMF | N/A |

FIG.4

| hydrolysate | concentration(g/L) |
|---|---|
| Glucose | 6.20 |
| Xylose | 25.29 |
| Arabinose | 7.57 |
| Acetic acid | 3.59 |
| Furfural | 0.29 |
| HMF | 0.05 |

FIG. 7

METHOD OF CULTIVATING YEAST FOR ENHANCING PENTITOL PRODUCTION

CROSS REFERENCE TO RELATED PATENT APPLICATIONS

This application claims priority from Taiwan Patent Application No. 098136801, filed in the Taiwan Patent Office on Oct. 30, 2009, entitled "Method of Cultivating Yeast for Enhancing Pentitol Production," and incorporates the Taiwan patent application in its entirety by reference.

TECHNICAL FIELD OF THE DISCLOSURE

The present disclosure relates to a method of cultivating yeast; more particularly, relates to cultivating the yeast for enhancing production yield of pentitol bioconversion from xylose in a lignocellulosic hydrolysate.

DESCRIPTION OF THE RELATED ARTS

Bioethanol is a potential biofuel for replacing gasoline. The cellulosic ethanol uses non-food lignocellulosic materials which have the advantages of abundance and wide varieties of sources worldwide that do not conflict with food shortage. The lignocellulosic materials may be agricultural/forestry waste like wood, bagasse, rice straw, corn stover, wheat straw, etc.; herbaceous biomass like silvergrass, napiergrass, etc.; or municipal waste like pulp waste. Using the lignocellulosic materials also has effects on reducing carbon emission and increasing net energy production. Thus, the technique of lignocellulosic materials based ethanol production has become the most promising to produce biofuel.

In general, lignocellulosic materials contains 60~80% of cellulose and hemicellulose and 15~25% of lignin. After converting cellulose and hemicellulose into hexose (mainly glucose) and pentose (mainly xylose) through a saccharification process respectively, these monosaccharides can be further converted into ethanol through microbial fermentation. In the other hand, on transforming cellulose into ethanol, diluted-acid hydrolysis pretreatment is usually used to break down hemicellulose into xylose. A certain ratio of raw material and an aqueous solution are firstly mixed and filled into a reactor, and then 1% to 2% (w/w) of diluted-acid is added under high-temperature and high-pressure conditions for reacting a few minutes. The xylose-rich hydrolysate thus obtained for fermentation has high concentration of sulfate, which may affect the ability of yeast on transforming xylose into ethanol. Moreover, the diluted-acid hydrolysis pretreatment may simultaneously generate fermentation inhibitors like acetic acid, furfural, hydroxymethyl furfural, etc., which could further affect the fermentation ability of the yeast. Therefore, the xylose-rich hydrolysate is usually proceeded with the overliming process to remove furfural and sulfate as to reduce the inhibition of the hydrolysate for microorganism fermentation.

Due to the technique for cellulosic ethanol is still under developing, the high production cost leads to its uncompetitiveness in the market place. There are still some difficulties in the current xylose-to-ethanol process such as production loss, low production yield and high energy consumption for ethanol recovery, thus many of the cellulosic ethanol pilot plants do not utilize xylose for ethanol production. Thus, the future trend for commercialization of cellulosic ethanol production is based on the process of cellulose-to-ethanol and in combination of high-valued chemical byproduct production from hemicellulose, as for upgrading the current ethanol production process to become a biorefinery platform Pentitol like xylitol, arabitol and ribitol is a kind of rare sugar, which exists in nature with a relatively low amount. It can be found in the composition of some vegetables and fruits, also is one of the intermediate metabolites in the sugars metabolism of mammal. Therein, arabitol can be used as a food additive or sweetener; and, ribitol is a vital material for synthesizing vitamin B2. However, xylitol attracts most of the global attention in recent years. It is mainly because xylitol is a natural sweetener having equivalent sweetness to sucrose with the calorie of merely 60% of sucrose. Hence, Except for the great help in preventing dental caries, xylitol is widely used in clinical as substitute of sucrose in the nutrition and replacing sucrose in foods for diabetics. As xylitol an example, the current industrial method for mass production uses the acid-pretreated xylose-rich lignocellulosic hydrolysate for raw material. Following the chemical synthesis is used that the xylose-rich hydrolysate is hydrogenated at high temperature and high pressure with the catalysis of nickel metal. However, the xylitol produced by the chemical synthesis with only a yield about 40~50% and also the complex procedure requires great amount of energy consumption.

Accordingly, a competitive method is to use microorganism in a bioconversion way of directly fermenting lignocellulosic hydrolysate to produce pentitol. In which by using the naturally occurring xylose-fermenting microorganism, the xylose is directly converted into pentitol through the physiological metabolism of the microorganism. Not only the risk of heavy metal contamination in the chemical method is avoided, but also the energy consumption is low.

In fact, some yeasts for producing pentitol are revealed, mainly the recombinant microorganisms (Toivari M. H., et al., 2007, Metabolic Engineering of Saccharomyces cerevisiae for Conversion of D-Glucose to Xylitol and Other Five-Carbon Sugars and Sugar Alcohols, Applied and Environmental Microbiology, p. 5471-5476). Although the yeast of *Candida* sp. can produce xylitol in high yield, the yeast does not produce other pentitols like arabitol and ribitol at the same time. Hence, the prior arts do not fulfill all users' requests on actual use.

SUMMARY OF THE DISCLOSURE

The main purpose of the present disclosure is to provide a yeast of *Pichia stipitis* as a fermentative microorganism with enhanced production yield of pentitols (xylitol, arabitol, ribitol) converted from xylose either in a overliming-detoxified or non-detoxified lignocellulosic hydrolysate.

The second purpose of the present disclosure is to provide a method for microorganism fermentation of lignocellulosic hydrolysate without detoxification process, as to avoid the requirement for hydrolysate detoxification as well as the investment cost for detoxification facilities, while the enhanced pentitol production yield of a non-detoxified hydrolysate is higher then that of an overliming-processed hydrolysate.

The other purpose of the present disclosure is to provide a yeast not only producing pentitol including xylitol, arabitol and ribitol; but also converting xylose into ethanol, which can be followed with ethanol recovery and concentration to obtain cellulosic ethanol as a fuel for vehicles.

To achieve the above purposes, the present disclosure is a method of cultivating yeast for enhancing pentitol production, comprising steps of: (a) adding acetic acid into an adaptation medium that is a mix of the pH 5.0 of NaOH-neutralized lignocellulosic hydrolysate and synthetic xylose medium; (b) subculturing a yeast of *Pichia stipitis* as a fermentative microorganism at least 5 generations in the adaptation medium and then increasing the acetic acid concentration to 3.0 g/L and 4.0 g/L while the xylose concentration of the adaptation medium is kept the same; and (c) culturing the yeast at least 25 generations in the adaptation medium having the acetic acid concentration of 4.0 g/L, where the synthetic xylose medium is a solution having xylose, yeast extract and peptone; and where the yeast produces pentitol and is cultured in an adaptation medium having an acetic acid concentration between 2.0 g/L and 4.0 g/L. Accordingly, a novel method of cultivating yeast for enhancing pentitol production is obtained.

BRIEF DESCRIPTIONS OF THE DRAWINGS

The present disclosure will be better understood from the following detailed description of the preferred embodiments according to the present disclosure, taken in conjunction with the accompanying drawings, in which FIG. 1 is the flow view showing the preferred embodiment according to the present disclosure;

FIG. 4 is the view showing the composition of the overliming-detoxified hydrolysate;

FIG. 7 is the view showing the composition of the NaOH-neutralized (non-detoxified) hydrolysate.

DESCRIPTION OF THE PREFERRED EMBODIMENT

The following description of the preferred embodiments is provided to understand the features and the structures of the present disclosure.

Figure 1:
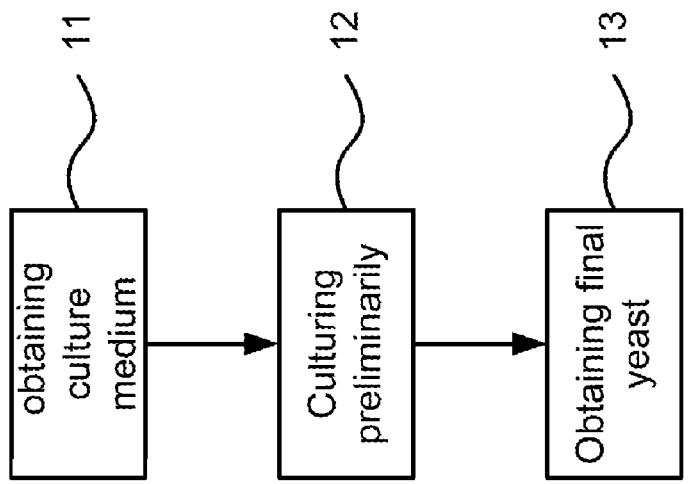

Please refer to FIG. 1, which is a flow view showing a preferred embodiment according to the present disclosure. As shown in the figure, the present disclosure is a method of cultivating yeast for enhancing pentitol production, comprising the following steps:

(a) Obtaining adaptation medium 11: Acetic acid is added into a lignocellulosic hydrolysate. The lignocellulosic hydrolysate is a xylose-rich solution and is neutralized with an alkali agent like NaOH to make the hydrolysate become weakly acidic (pH5.0). Then the hydrolysate is mixed with a synthetic xylose medium to obtain a yeast adaptation medium, where the synthetic xylose medium has a final volume ratio of 20% in the adaptation medium. Therein, the adaptation medium has an initial xylose concentration of 40 grams per liter (g/L) and an acetic acid concentration of 2.5 g/L; and, the synthetic xylose medium is a medium comprising xylose, yeast extract and peptone.

(b) Culturing preliminarily 12: A yeast of *Pichia stipitis* as a fermentative microorganism is cultured for at least 5 generations in the adaptation medium. After the yeast is subcultured at least 5 generations, the acetic acid concentration in the adaptation medium is increased to 3.0 g/L and 4.0 g/L while the xylose concentration is kept the same.

(c) Obtaining the final adapted yeast 13: At last, the yeast is cultured for at least 25 generations in the adaptation medium having the acetic acid concentration of 4.0 g/L. Thus, the yeast having enhanced pentitol productivity is obtained.

Application of the present disclosure in a non-detoxified or overliming-treated lignocellulosic hydrolysate for having enhanced production of pentitol, where the pentitol comprises xylitol, arabitol and ribitol. Therein, the yeast is cultured in an adaptation medium having an acetic acid concentration between 2.0 g/L and 4.0 g/L; and, the carbon source of the adaptation medium is selected from the group of glucose, xylose or xylose-rich hydrolysate.

The xylose-rich hydrolysate can be the lignocellulosic hydrolysates obtained by pretreatment of biomass materials such as rice straw, sugarcane bagasse, silvergrass, napiergrass, pineapple peel, switchgrass, wood or bamboo, where said material is pretreated through: (1) twin-screw extruder squeezing with acid mixed while in coordination with hot-water wash; or (2) diluted-acid catalyzed hydrolysis; or (3) acid-impregnated steam explosion process or other dilute-acid pretreatment process.

Figure 2:
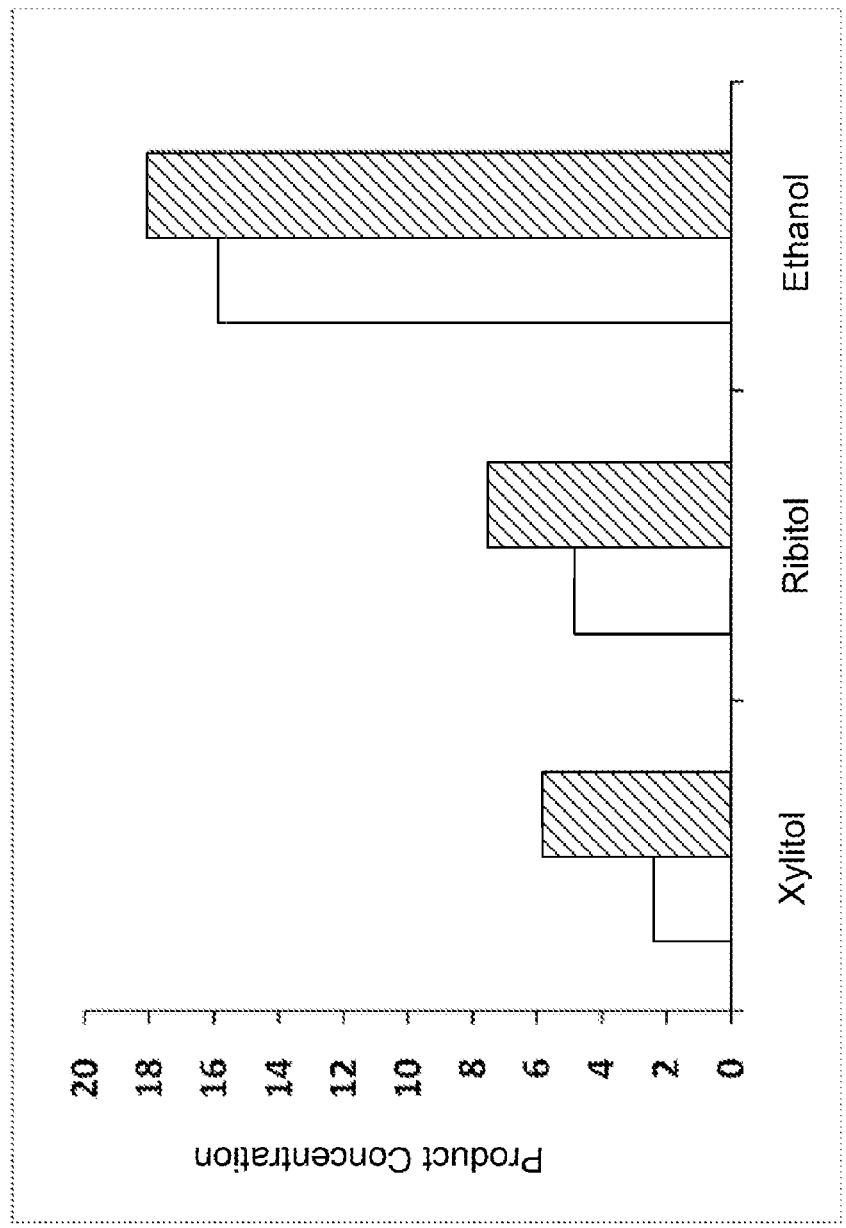
FIG. 2 is the view showing the pentitol product concentrations in the synthetic xylose medium, the empty bar represents "the original yeast" and the slash bar represents "the cultured yeast"

Please refer to FIG. 2, which is a view showing pentitol product concentration from fermentation of the synthetic xylose medium. As shown in the figure, the cultured yeast according to the present disclosure is used for fermentation of a synthetic xylose medium with an initial xylose concentration of 6% (w/w). The fermentation temperature is controlled at 30° C., the agitation of the incubator is maintained at 100~150 rpm, and the ratio of the inoculum size of the culture and the volume of the fermentation medium is 1:6 (v/v). As the result shows, the slash portions of the figure indicates 2.1 times of xylitol yield and 1.5 times of ribitol yield are obtained using the yeast cultured according to the present disclosure. It demonstrates the yeast that has been cultured with the method of the present disclose indeed have the enhanced xylos-to-pentitol conversion yields.

Figure 3:
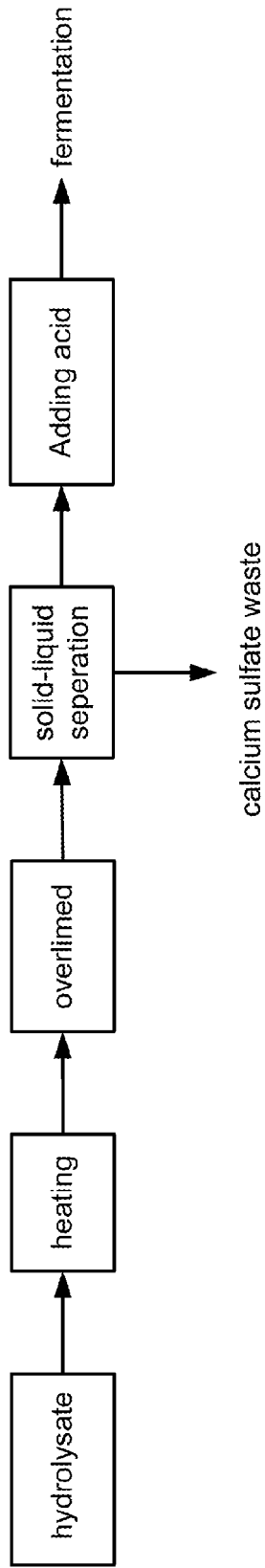
FIG. 3 is the flow view showing the overliming detoxification process of lignocellulosic hydrolysate.
Figure 5:
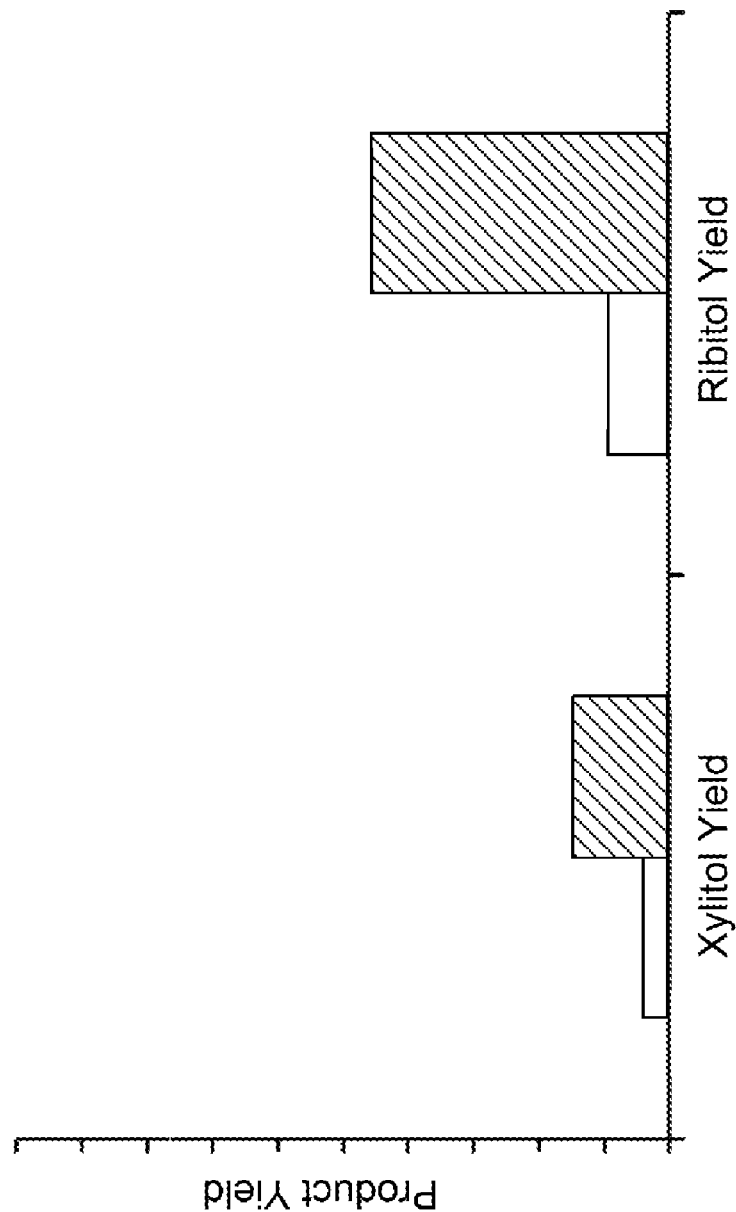
FIG. 5 is the view showing the pentitol production yield of the overliming hydrolysate, the empty bar represents "the original yeast" and the slash bar represents "the cultured yeast"

Please refer to FIG. 3 to FIG. 5, which are a flow view showing the overliming process of xylose-rich hydrolysate; a view showing the composition of the overliming-processed hydrolysate; and a view showing pentitol yields of the over-liming-processed hydrolysate. As shown in the figures, a cultured yeast obtained according to the present disclosure is used to produce pentitol from an overliming-processed rice straw hydrolysate, where the overliming-processed rice straw hydrolysate is obtained through heating, over-liming, solid-liquid separation, pH-value adjustment with acid agent, and calcium sulfate waste removal.

The xylose-rich rice straw hydrolysate is obtained by a pretreatment facility equipped with a twin-screw extruder and a washing reactor. In the reaction, the suitably sized of rice straw is firstly structurally decomposed by the twin-screw extruder, in which the dilute acid concentration is 1-3% (w/w), the screw speed is 40 rpm, the reaction temperature is 120-130° C., the reaction time is 10-20 min, and the ratio of the dry weight of the feeding rice straw and the aqueous solution is about 50:100. After being treated with the extruder, the rice straw is introduced to the washing reactor, into which an appropriate amount of steam is applied, such that the ratio of the dry weight of the rice straw and the aqueous solution is decreased to about 30:100, and at the same time, the reaction temperature is raised to 160° C., and at this temperature, the reactant is boiled for 20 min. Then, the rice straw and the aqueous solution after reaction are discharged, and separated in a solid-liquid separation equipment. The obtained aqueous solution is the xylose-rich hydrolysate, and the main composition is as shown in FIG. 4.

The pH value of the overliming-processed rice straw hydrolysate is adjusted to 5.0 for fermentation. The fermentation temperature is controlled at 30° C., the agitation of the incubator is maintained at 100~150 rpm, and the ratio of the inoculum size of the culture and the volume of the fermentation medium is 1:6 (v/v). As a result shows in FIG. 5, the slash portions of the figure indicates 3.6 times of xylitol yield and 4.9 times of ribitol yield are obtained using the yeast cultured according to the present disclosure. Thus is proved that the yeast cultured according to the present disclosure can be used for producing pentitols with enhanced yields from overliming-processed rice straw hydrolysate.

Figure 6:
FIG. 6 is the flow view showing the non-detoxification process of lignocellulosic hydrolysate.
Figure 8:
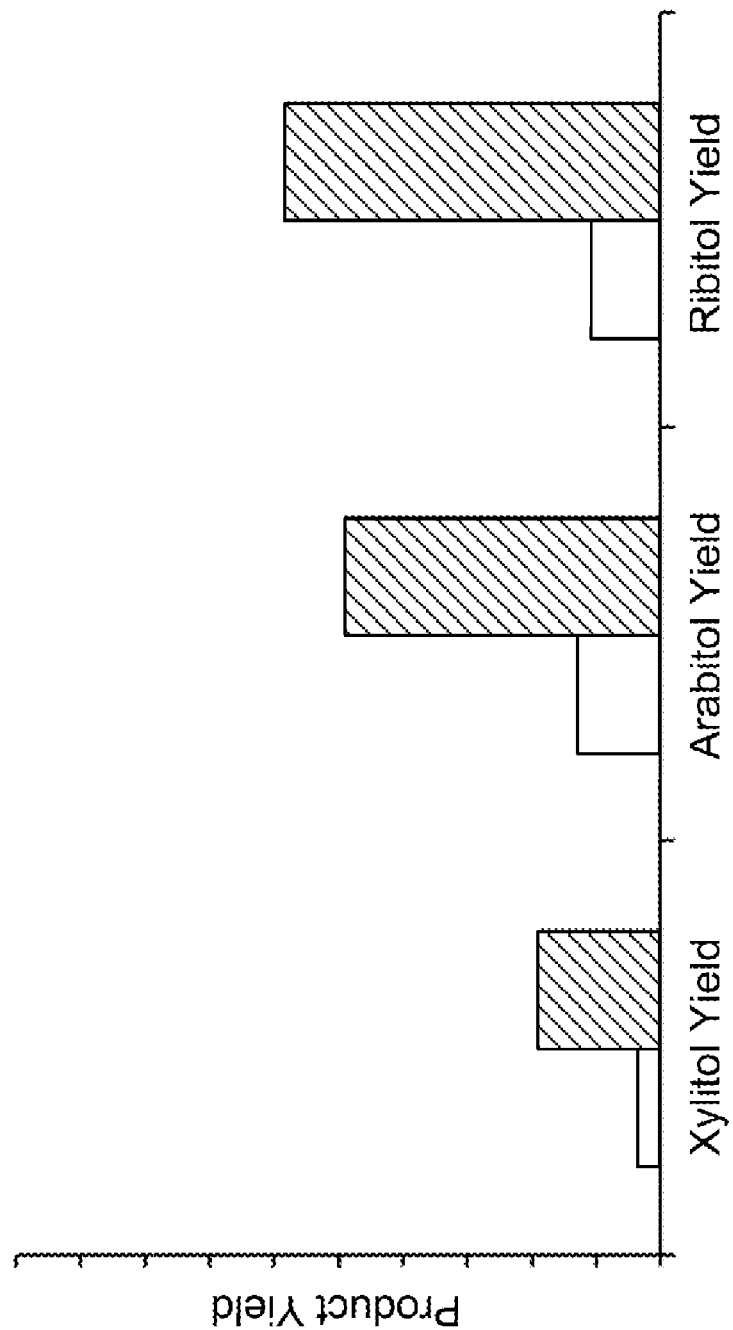
FIG. 8 is the view showing the pentitol yield of the NaOH-neutralized hydrolysate, the empty bar represents "the original yeast" and the slash bar represents "the cultured yeast"

Please refer to FIG. 6 to FIG. 8, which are a flow view showing the NaOH-neutralized process of xylose-rich hydrolysate without detoxification; a view showing composition of a NaOH-neutralized hydrolysate; and a view showing pentitol yields of the NaOH-neutralized hydrolysate. As shown in the figures, a xylose-rich rice straw hydrolysate is neutralized with NaOH to obtain the pH value of 5.0.

Composition of the NaOH-neutralized hydrolysate is shown in FIG. 7. The fermentation temperature is controlled at 30° C., the agitation of the incubator is maintained at 100~150 rpm, and the ratio of the inoculum size of the culture and the volume of the fermentation medium is 1:6 (v/v). As the result shows in FIG. 8, the slash portions of the figure indicates 5.5 times of xylitol yield, 3.8 times of arabitol yield and 5.5 times of ribitol yield are obtained using the yeast cultured according to the present disclosure. It demonstrates the yeast that has been cultured with the method of the present disclose indeed have the enhanced xylos-to-pentitol conversion yields. Thus is proved that the yeast cultured according to the present disclosure can be used in the non-detoxified rice straw hydrolysate to produce pentitol with high yield, which yield enhanced is remarkable than that for an overliming-processed rice straw hydrolysate.

Accordingly, The present disclosure can enhance pentitol yield on fermenting lignocellulosic hydrolysate, where the pentitol yield enhanced from a non-detoxified hydrolysate is higher then that of an overliming-processed hydrolysate. Hence, it is non-necessity of overliming detoxification for lignocellulosic hydrolysate. Furthermore, the investment cost for detoxification can be saved. In addition, the yeast obtained through the present disclosure not only produces pentitol including xylitol, arabitol and ribitol; but also converts xylose into ethanol, which can be followed with ethanol recovery and concentration to obtain cellulosic ethanol as fuel for vehicles.

To sum up, the present disclosure is a method of cultivating yeast for enhancing pentitol production, where *Pichia stipitis* is the fermenting microorganism cultivated according to the present disclosure. The yeast is to be used in the non-detoxified or overliming-processed lignocellulosic hydrolysate for enhancing pentitol yield of converting from xylose in the lignocellulosic hydrolysate.

The preferred embodiment herein disclosed is not intended to unnecessarily limit the scope of the disclosure. Therefore, simple modifications or variations belonging to the equivalent of the scope of the claims and the instructions disclosed herein for a patent are all within the scope of the present disclosure.

What is claimed is:

1. A method of cultivating yeast for enhancing pentitol production, wherein *Pichia stipitis* is the fermenting microorganism cultivated, the method comprising:
    providing an adaptation medium having an acetic acid concentration between 2.0 g/L and 4.0 g/L;
    culturing a yeast of *Pichia stipitis* as a fermentative microorganism in the adaptation medium; and
    after the yeast has been cultured for at least 25 generations, applying the yeast in a non-detoxified or overliming-treated lignocellulosic hydrolysate to provide enhanced production of pentitol, wherein pentitol production by *Pichia stipites* that has been cultivated in the adaptation medium is higher than pentitol production by *Pichia stipitis* that is not cultivated in the adaptation medium.

2. The method according to claim 1, wherein the pentitol comprises xylitol, arabitol and ribitol.

3. The method according to claim 1, wherein a carbon source of the cultured yeast is selected from the group consisting of glucose, xylose, and xylose hydrolysate of a lignocellulosic biomass material.

4. The method according to claim 1, wherein, an alkali agent is previously added into the non-detoxified lignocellulosic hydrolysate to adjust a pH value between 4.5 and 7.0.

5. The method according to claim 1,wherein a xylose-rich hydrolysate is obtained after pretreatment of lignocellulosic materials selected from the group consisting of rice straw, sugarcane bagasse, silvergrass, napiergrass, pineapple peel, switchgrass, wood, bamboo, and other lignocellulosic biomass materials.

6. The method according to claim 5, wherein the pretreatment is selected from the group consisting of a process by twin-screw extruder for mixing acid combined with a hot water washing process, a dilute acid catalyzed hydrolysis method, an acid-impregnated steam explosion pretreatment, and other dilute acid pretreatment process.

* * * * *